United States Patent
Go Boncan et al.

(10) Patent No.: US 9,429,558 B2
(45) Date of Patent: Aug. 30, 2016

(54) MULTI-FUNCTION TESTING APPARATUS FOR CEMENT AND METHODS OF USING THE SAME

(75) Inventors: Virgilio C. Go Boncan, Spring, TX (US); Robert S. Martin, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 787 days.

(21) Appl. No.: 13/533,760

(22) Filed: Jun. 26, 2012

(65) Prior Publication Data
US 2013/0340505 A1   Dec. 26, 2013

(51) Int. Cl.
*G01N 33/38* (2006.01)

(52) U.S. Cl.
CPC .................................. *G01N 33/383* (2013.01)

(58) Field of Classification Search
CPC .................................................. G01N 33/383
USPC .............. 73/37, 38, 760, 788–790, 794–796, 73/803, 818, 821, 826, 64.41, 149, 429, 73/865.6, 866; 249/66.1, 78, 82, 158; 374/55, 56
See application file for complete search history.

(56) References Cited

U.S. PATENT DOCUMENTS

| | | | |
|---|---|---|---|
| 4,377,087 A * | 3/1983 | Rodot | G01N 29/024 73/594 |
| 5,741,971 A | 4/1998 | Lacy | |
| 6,817,238 B2 * | 11/2004 | Go Boncan | G01N 33/383 73/149 |
| 7,191,663 B2 | 3/2007 | Go Boncan et al. | |
| 7,240,545 B1 * | 7/2007 | Jennings | G01F 22/00 73/149 |
| 7,552,648 B2 * | 6/2009 | McMechan et al. | 73/803 |
| 7,942,064 B2 * | 5/2011 | Maki, Jr. | G01N 29/036 73/803 |
| 8,236,100 B2 * | 8/2012 | Le Roy-Delage | G01N 33/383 106/724 |
| 8,601,882 B2 * | 12/2013 | Gray | G01N 3/24 73/803 |
| 2005/0126300 A1 * | 6/2005 | Go Boncan | G01N 3/08 73/803 |
| 2008/0178683 A1 * | 7/2008 | Heathman | G01N 3/24 73/803 |
| 2011/0094295 A1 * | 4/2011 | Meadows | G01N 3/08 73/38 |
| 2011/0107848 A1 | 5/2011 | Le Roy-Delage et al. | |
| 2012/0072133 A1 * | 3/2012 | Norwood | G01D 21/02 702/45 |

* cited by examiner

*Primary Examiner* — Hezron E Williams
*Assistant Examiner* — Hoang Nguyen
(74) *Attorney, Agent, or Firm* — John Wilson Jones; Jones & Smith, LLP

(57) ABSTRACT

A multi-function testing apparatus contains a test cell, a piston positioned within the test cell and an adjustable piston depth-setting rod. The testing apparatus may be used to assess carbon dioxide resistance and hydraulic bonding strength of a set cement as well as to evaluate the self-healing capabilities of a set cement. Testing on the set cement may be conducted at simulated downhole conditions.

13 Claims, 10 Drawing Sheets

MULTI-FUNCTION TESTING APPARATUS FOR CEMENT AND METHODS OF USING THE SAME

FIELD OF THE INVENTION

The invention relates to a multi-function apparatus for testing set cements at temperatures and pressures simulating those in a subterranean reservoir. The invention further relates to methods of using the multi-function testing apparatus.

BACKGROUND OF THE INVENTION

During construction of oil and gas wells, a rotary drill is typically used to bore through subterranean formations of the earth to form a borehole. As the rotary drill bores through the earth, a drilling fluid or mud is circulated through the borehole. Drilling fluids are usually pumped from the surface through the interior of the drill pipe. By continuously pumping the drilling fluid through the drill pipe, the drilling fluid can be circulated out the bottom of the drill pipe and back up to the well surface through the annular space between the wall of the well bore and the drill pipe.

Once the wellbore has been drilled, casing is lowered into the wellbore. A cement slurry is then pumped into the casing and a plug of fluid, such as drilling mud or water, is then pumped behind the cement slurry in order to force the cement up into the annulus between the exterior of the casing and the borehole. The cement slurry is then allowed to harden as a sheath. The cement sheath then holds the casing in place. The well is subsequently stimulated in order to enhance the recovery of oil or gas from the reservoir.

During well treatment operations, including stimulation operations, cement sheaths are subjected to axial, shear and compressional stresses induced by vibrations and impacts. In particular, stress conditions may be induced or aggravated by fluctuations or cycling in temperature or fluid pressures. In addition, variations in temperature and internal pressure of the wellbore pipe string may result in radial and longitudinal pipe expansion and/or contraction. This tends to place stress on the annular cement sheath existing between the outside surface of the pipe string and the inside formation surface or wall of the wellbore. Such stresses lead to cracking and/or disintegration of the cement sheath.

Not only must the cement slurry have a pumpable viscosity, acceptable fluid loss control, minimal settling of particles and the ability to set within a practical time, the cement mix and the properties of the cement slurry must be carefully selected in order to minimize or eliminate cracking of the cement sheath. As such, the cement mix and the slurry containing the mix must be tailored in order for the cement sheath to withstand those axial stresses, shear stresses and compressional stresses encountered under in-situ wellbore conditions. Further, the components of the cement mix and the cement slurry must be selected such that, when hardened, the cement sheath is not brittle since brittleness causes cracking of the sheath.

Thus, it has become increasingly important for service providers to provide to well operators cement mixes capable of withstanding specific downhole conditions well and specific operating conditions which the well is to be subjected.

Several testing methods have been developed to date to test physical properties of cured cements. For example, ASTM International has established the Standard Test Method for Flexural Strength of Concrete (Using Simple Beam With Center-Point Loading), Designation No. C 293-02. This test method purports to accurately determine the flexural strength of a set cement specimen by the use of a simple beam with center-point loading. The method employs a load-applying block and two specimen support blocks wherein force is applied perpendicular to the face of the specimen until the specimen fails. The modulus of rupture is calculated as:

$$R = 3PL/2bd^2 \quad (1)$$

wherein:
R=Modulus of rupture, psi, or MPa,
P=maximum applied load indicated by the testing machine, lbf, or N,
L=span length, in., or mm,
b=average width of the specimen at the fracture, in., or mm; and
d=average depth of the specimen a the fracture, in., or mm.

However, the method only provides a modulus of rupture based on a perpendicular force being applied in surface ambient conditions. The method therefore fails to simulate the stresses encountered in the higher temperature and pressure conditions of the wellbore environment.

Additional standards have been developed for testing cement. For example ASTM International Standard Test Method for Flexural Strength of Hydraulic-Cement Mortars, Designation No. C 348-02 provides a centerpoint loading such that forces are applied to the specimen in a vertical direction to determine the flexural strength from the total maximum load as follows:

$$S_f = 0.0028P \quad (2)$$

wherein:
$S_f$=flexural strength, Mpa, and
P=total maximum load, N.

This method only provides a flexural strength based on a vertical force being applied in surface ambient conditions to cause a total maximum load. This method therefore also fails to simulate the stresses encountered in the higher temperature and pressure conditions of the wellbore environment.

Mechanical properties of set cement have further been predicted using a curing chamber which purports to simulate downhole wellbore conditions. In most cases, after hardening of the slurry the test temperature and pressure are slowly decreased to accommodate the safe removal of test sample from the curing chamber. In light of such changing conditions, the data is less than accurate.

A testing protocol is desired which does not introduce experimental errors into the procedure. In particular, a testing protocol is desired for assessing mechanical properties of a cement sheath at simulated conditions and at conditions found in the wellbore environment.

A need exists for a testing method for hardened cements under conditions which simulate conditions found in a wellbore environment. Testing methods under these conditions will provide the requisite data for optimizing the properties of cementitious slurries for rendering suitable hardened cements at in-situ stress conditions.

SUMMARY OF THE INVENTION

The multi-function testing apparatus described herein may be used to assess carbon dioxide resistance and hydraulic bonding strength of set cements as well as to evaluate the self-healing capabilities of a test cement. Testing on the set cements and hardening of the cements within the testing apparatus are conducted at simulated downhole conditions of temperatures up to 500° F. and pressures up to 3000 psi. Since physical dimensions of set cements change rapidly with test temperatures and test pressures, the testing method provides more accurate data since testing is conducted at in-situ reservoir pressures and temperatures. Further, the testing of the set cement may be conducted under controlled flow rates of formation fluids. The formation fluid may be crude oil, hydrocarbon gas or combinations, carbon dioxide, hydrogen sulfide gas, fresh water, brine, steam and the like.

The testing apparatus contains a test cell which also functions as the curing chamber for a cement slurry containing the cement mix. The test cell further contains an inlet port and an outlet port for transporting formation fluids into and away from the test cell at elevated pressures. In addition, the testing apparatus may include a top cover and a bottom cover for the test cell.

The testing apparatus further contains a piston which is appropriately sized to fit within the test cell. An adjustable piston depth-setting rod (APSR) and a piston depth positioning locator (PDPL) may be mountable to the testing apparatus through the top cover. Two displacement transducers may be mountable on the outside of the testing apparatus. One of the displacement transducers measures the position of the APSR and the vertical movement of the piston as it advances during testing. The other displacement transducer measures the setting depth and the longitudinal motion of the piston.

In one embodiment of the invention, the multi-function testing apparatus described herein may be used for characterizing the self-healing properties of a set cement. Self-healing cements are adaptive cement systems in that they are capable of self-healing in order to compensate for changes which may occur downhole.

The testing method described herein may further be used to identify an acceptable cement based on actual downhole conditions at anticipated fracture widths defined by the operator.

In the testing of a self-healing cement, the method defined herein includes inducing a fracture or crack in the hardened cement in the test cell. After the cement is allowed to seal, conditions are selected such that the fracture conforms to a designated width. The maximum pressure required to break the seal at a fixed temperature is then determined.

The multi-function testing apparatus further provides the ability to monitor timing of inducement of the fracture in the set cement at a predetermined width.

In another embodiment of the invention, the multi-function testing apparatus described herein may be used to test carbon dioxide resistance of an unfractured set cement. For instance, the piston may be used to determine the corrosion rate caused by carbonic acid. Carbonic acid is injected into the test cell through the inlet port and the amount of water exiting through the outlet port is monitored. The effect of corrosion rate to cement/casing bonding strength is thus determined.

In still another embodiment of the invention, the multi-function testing apparatus described herein may be used for testing two types of cement bonding strength; the hydraulic bonding strength and shear bonding strength of a set cement. This may be achieved by pushing the piston embedded in the center of the set cement. The amount of force required to break the interfacial adhesion of the cement to the piston is recorded.

BRIEF DESCRIPTION OF THE DRAWINGS

In order to more fully understand the drawings referred to in the detailed description of the present invention, a brief description of each drawing is presented, in which.

DETAILED DESCRIPTION OF THE PREFERRED EMBODIMENTS

Figure 1:
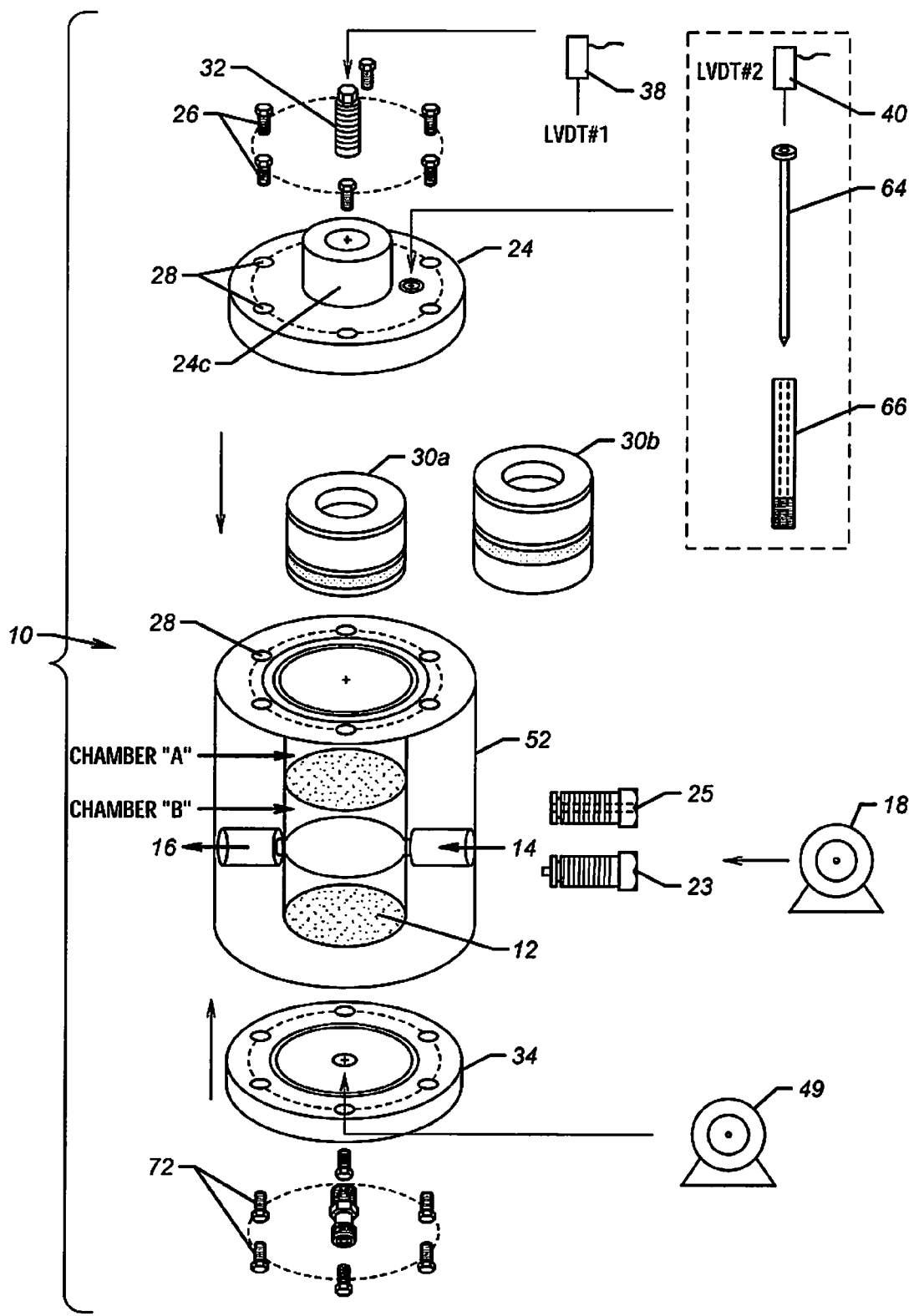
FIG. 1 is an exploded view of an exemplary multi-function testing apparatus.
Figure 2:
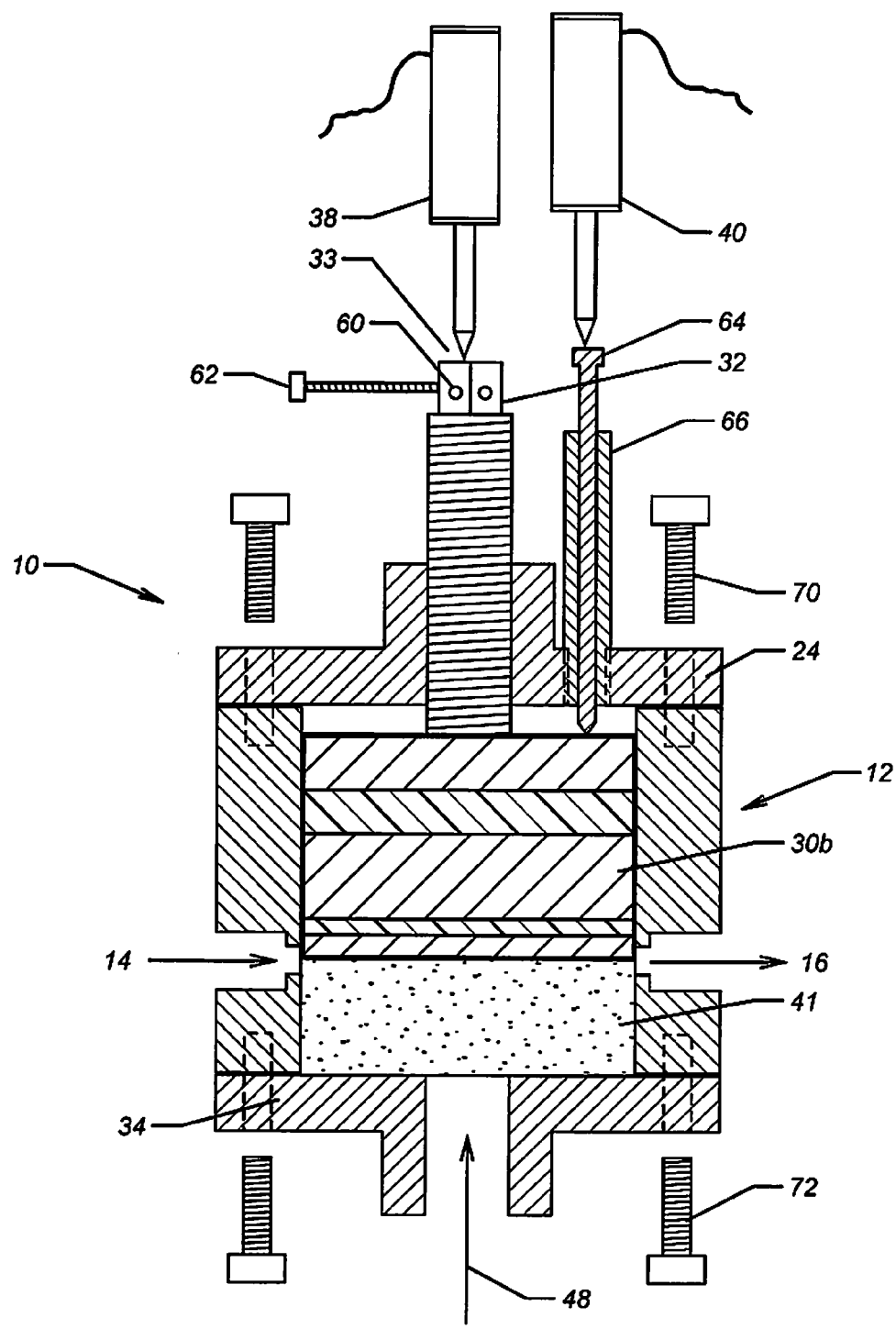
FIG. 2 is a front view of an exemplary multi-function testing apparatus especially useful in testing the ability of a self-healing cement to seal off the micro-annulus between the casing and the cement or for determining the hydraulic bonding strength of cement to metal. This testing apparatus may also be used for measuring the carbon dioxide resistance of a hardened cement.
Figure 3:
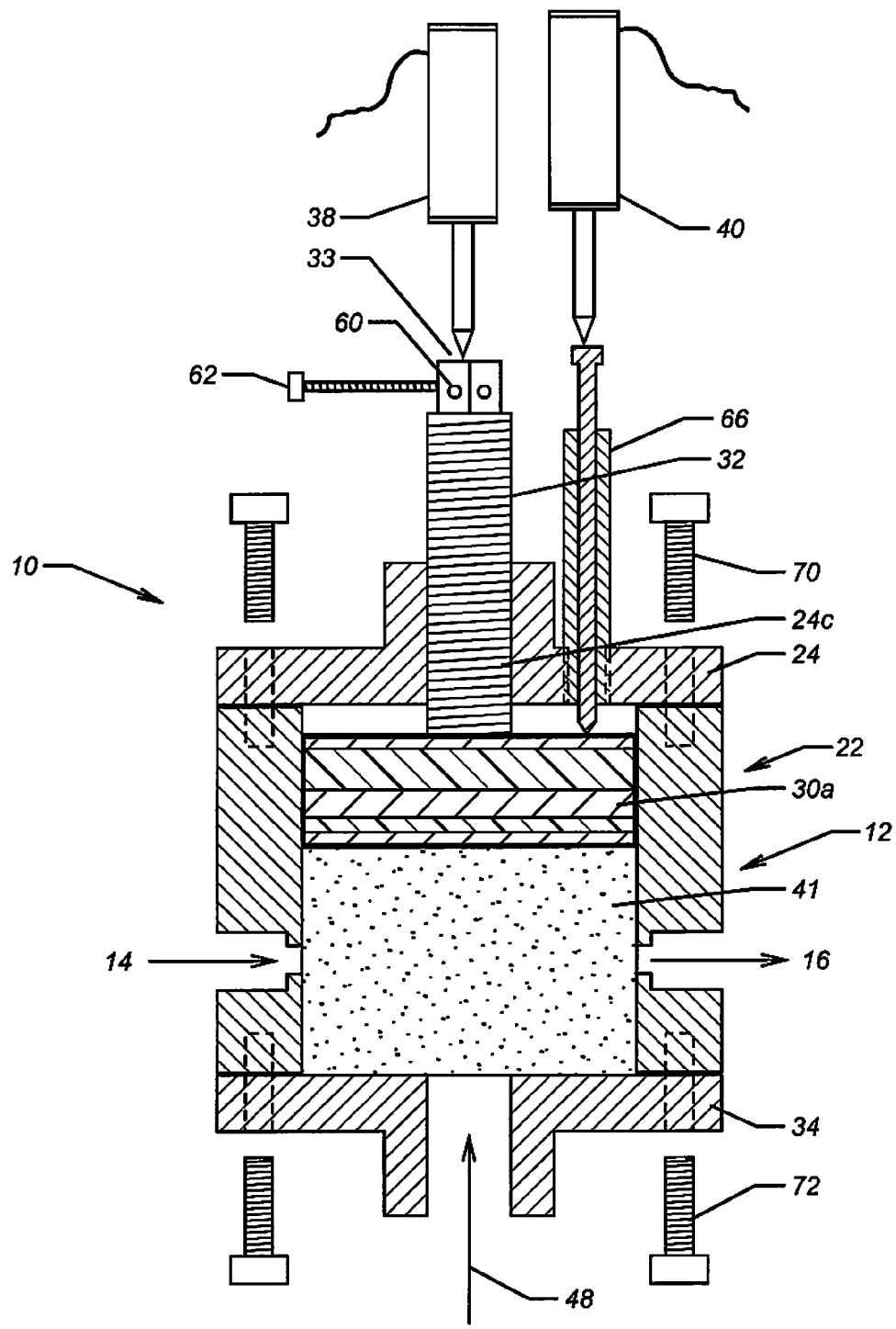
FIG. 3 is a front view of an exemplary multi-function testing apparatus especially useful in measuring the mechanical shear bonding strength of a set cement or self-healing properties of set cement after a crack has been induced.

The multi-function testing apparatus defined herein is capable of performing a multitude of tests on set cement. In each of the tests, a fracture is induced in the hardened cement. Representative configurations of the multi-function testing apparatus 10 are set forth in FIGS. 1, 2 and 3. FIG. 1 is an exploded view of the multi-function testing apparatus. The embodiment illustrated in FIG. 2 has particular applications in testing the healing capacity of a self-healing hardened or cured cement. In addition, FIG. 2 is useful for measuring hydraulic bonding strength as well as carbon dioxide resistance of a hardened cement. The embodiment illustrated in FIG. 3 is particularly useful in measuring the bonding strength of cements.

The parameters under which the cement mixes are tested are at simulated down-hole conditions (SDC) of temperatures up to 500° F. and pressures up to 3000 psi.

Referring to FIG. 1, testing apparatus 10 contains test cell 12. A cement slurry containing a cement mix is hardened in test cell 12. Test cell 12 further contains inlet port 14 and outlet port 16.

During the fracturing of the set cement, stage, hydraulic pressure enters inlet port 14 from precision pump 18 to induce the fracture. Representative precision pumps include high pressure plunger-type pumps having two types of control mode, a constant pressure or a constant volume flow at high pressures. Exemplary of such precision pumps are the Quizix Q5000 Pump Systems including model Q5200 a two-cylinder pump system for pumping of one fluid continuously.

Blank plugs 23 are inserted within inlet port 14 and outlet port 16 to prevent solids from filling and entering the port throats into test cell 12. The blank plugs are replaced with injection plugs 25 after the cement has set depending on the type of cement testings.

Top cover 24 is attachable to the outside rim of the uppermost portion of test cell 12 and is secured to testing apparatus 10 with fasteners 70. As shown in FIG. 1, a multitude of fasteners 26 extend through top cover 24 into receiving holes 28 in the top of test cell 12.

A piston is sized to snugly fit within the cavity of test cell 12. An adjustable piston depth-setting rod (APSR) 32 is mounted to testing apparatus 10 through top cover 24 and extends into test cell 12. FIG. 1 shows APSR 32 being mounted through raised cylinder 24c of top cover 24.

As illustrated in FIG. 2 and FIG. 3, the size of the piston may be dependent on the desired application of testing apparatus 10. FIG. 1 illustrates two types of pistons; the design of the pistons may be identical except piston 30b is slightly longer than piston 30a. In FIG. 2 the bottommost portion of piston 30b is illustrated as resting between inlet port 14 and outlet port 16 of test cell 12. FIG. 2 shows piston 30b as being longer than piston 30a. In FIG. 3, piston 30a is shown within test cell 12 as being positioned substantially above on the horizontal axis defined by inlet 14 and outlet port 16.

During assembly of the testing apparatus, the piston may be inserted into test cell 12 from the bottom until it is securely against the bottom of APSR 32. The inside wall of test cell 12 and the bottom of piston 30a or 30b are wiped clean to remove any trace of oil or grease to prepare for cement bonding to these surfaces.

Two displacement transducers (DT) 38 and 40 are mountable on the outside of testing apparatus 10. The displacement transducers are preferably spring loaded Linear Variable Displacement Transducers. DT 38 measures the position of APSR 32. DT 40 measures the setting depth of the piston at any time during cement curing or as it advances upwardly during crack inducing testing. DT 38 and DT 40 preferably have an inner spring which will push the armature downward and exert a small force against an object if mounted properly. This allows transducer 38 to automatically measure any vertical movement or adjustment of APSR 32 from top cover 24 while transducer 40 automatically measures any longitudinal motion of the piston at any time. Piston 30a or 30b resides inside testing apparatus 10 during testing. Bottom cover 34 consists of a port for applying the curing pressure.

The upper section of APSR 32 which extends to the outside testing apparatus 10 in FIG. 2 may have a hexagonal head for easy adjustment with standard open wrench. Turning the APSR either clockwise or counterclockwise correspondingly adjusts the depth setting of the piston either upwardly or downwardly inside the testing apparatus. In a preferred embodiment, each face on the hexagonal head has one drilled threaded hole or piston depth positioning locator (PDPL) 60. A machine screw or "limit screw" 62, typically 1.25 inches long, is threaded into PDPL 60 during a test run.

Push pin 64 extends from the top of the piston 30a or 30b to transducer DT 40. Push pin sleeve 66 is mounted on top cover 24. It serves as guide for push pin 64 to freely slide up or down during the test and also as reference setting position for the limit screw 62. Push pin 64 is secured on the top cover 24 within the rotational path of limit screw 62. APSR 32 is threaded through central top 24c to about $\frac{1}{16}$ to $\frac{3}{16}$ inches below central top 24c. To reduce experimental errors encountered on flat end surfaces, the lower end of push pin 64 typically is cone shaped. Push pin 64 freely slides through push pin sleeve 66 and physically transmits travel of piston 30 to displacement transducer 40 at any time during sample curing or testing.

Limit screw 62 is threaded to a first PDPL 60 and will lean against push pin 64. For illustration purposes, the first PDPL will be referred to as Point A. At Point A, limit screw 62 defines a limited boundary for APSR 32 to rotate. Conversely at this location it will also limit the range of travel for APSR 32. For purposes of illustration, consider that the testing apparatus contains five PDPLs—Positions A, B, C, D and E. When limit screw 62 is set on another PDPL location, another limited rotation boundary is delivered and the APSR will only travel to the new range offered. APSR 32 has the shortest travel if set on Position A and the deepest if set on Position E.

The cement slurry is preferably introduced by pouring the slurry into test cell 12 through the bottom without bottom cover 34 while in inverted position. As illustrated in FIG. 3, the testing fluid for mechanical shear bond strength test is injected through the bottom to port 48. Bottom cover 34 has a rubber "O" ring to seal the bottom cover 34 to the test cell 10. Bottom cover 34 is secured to test cell 12, curing pressure from pressure source 49 is introduced into test cell 12 through bottom port 48.

In conventional testing apparatus, test temperatures and pressures are slowly decreased after curing of the cement until conditions are safe for the removal of the set sample from the curing chamber. These steps introduce experimental errors into the analysis and thus provides less accurate data. The testing of the set cement by the invented method defined herein does not require the removal of the set cement from test cell 12.

Figure 4:
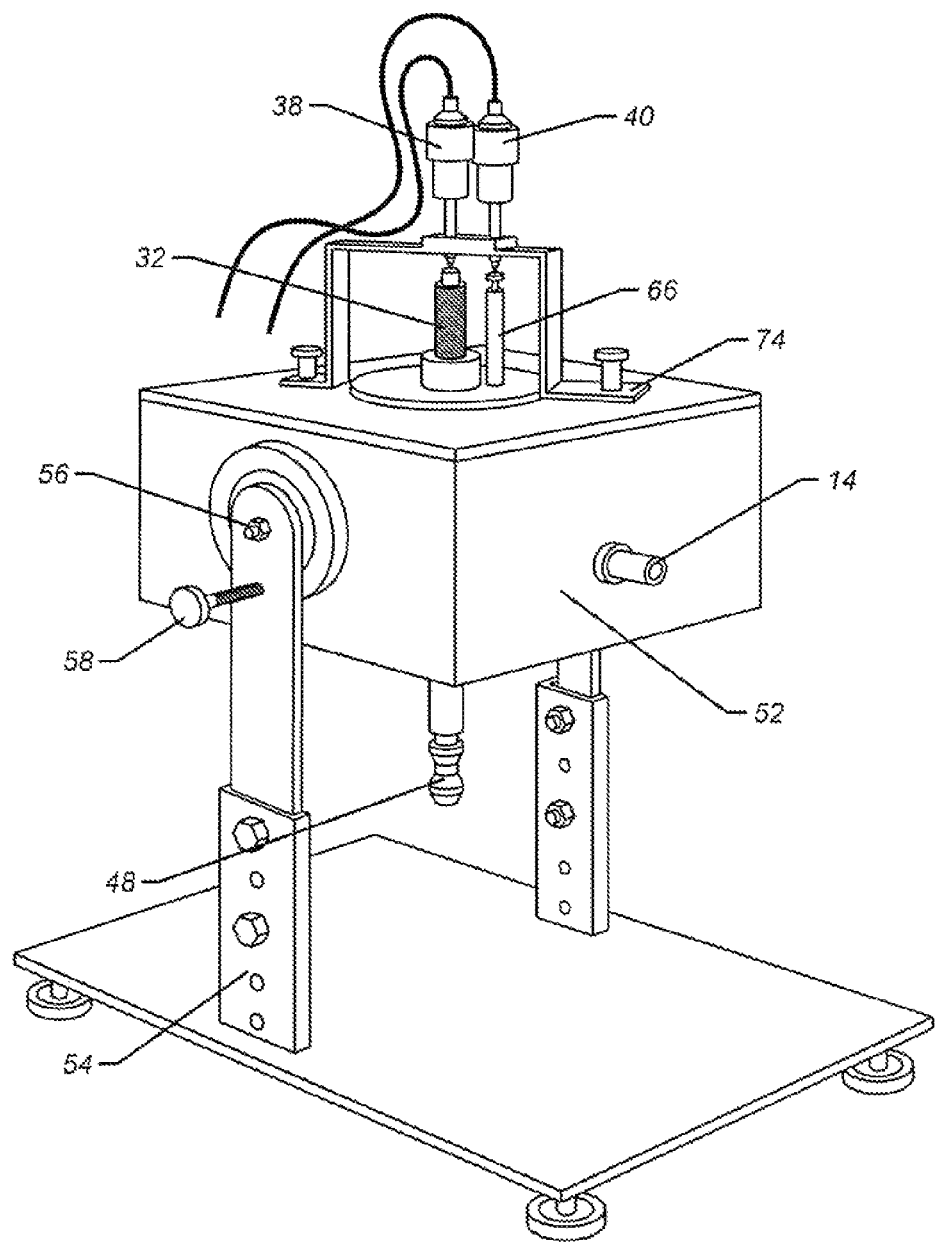
FIG. 4 is a side view of an exemplary testing apparatus which is capable of being inverted.

FIG. 4 illustrates an alternative embodiment of the invention wherein heating jacket 52 surrounds the test cell. Testing apparatus 10 may be elevated above the ground and supported by legs 54. Apparatus 10 is secured to the heating jacket 52 with safety lock 74 and may be inverted along by pivot 56. Lockpin 58 affixes testing apparatus 10 in place. After the cement slurry is introduced into test cell 12, the bottom cover 34 is secured to test cell 12 of testing apparatus 10. After the cement has set the assembly may be inverted such that displacement transducer 38 and displacement transducer 40 become the uppermost element of the testing apparatus. It will provide an easy access for adjusting to APSR 32.

Prior to introducing the cement slurry to test cell 12, blank plug 23 is preferably installed at inlet port 14 and outlet port 16 to ensure that the tunnel created between two ports is left open and free of set cement during the sample fracturing.

The cement slurry may then be poured into testing apparatus 10 through the bottom of test cell 12. The slurry is preferably puddled with a stirrer, such as a glass rod, to allow the air entrained in the slurry to escape. Bottom cover 34 is secured to testing apparatus 10 with fasteners 72. The slurry is then cured at pre-determined pressures and temperatures.

FIG. 2 is a representative testing apparatus for testing of self-healing cements in, for example, the micro-annulus. Thus, the apparatus of FIG. 2 may be used to test ability of the self-healing cement or other cement system to heal off or reduce fluid flow through the micro-annulus between the cement and the casing. In addition, FIG. 2 may be used to test the hydraulic bonding strength of the cement.

In the field, the self-repairing properties of self-healing cements are initiated when hydrocarbon fluids or other wellbore fluids originating from the formation come into contact with an exposed surface of the cement. As such, self-healing cements preserve the integrity of the cement sheath when the cement sheath is compromised by fractures or fissures. Typically, self-healing cements seal the fractures micro-annulus by swelling. The self-healing additives of the cement mix are embedded in the cement matrix during mixing and remain dormant until activated by formation fluids, such as crude oil, water, gas, steam, etc.

The testing apparatus assembly described herein may be used to measure the self-healing properties of a test cement mix at in-situ conditions. As such, the testing apparatus may be used to formulate a suitable self-healing cement mix or other types of cementing system.

The hydraulic pressure and fluid flow rate required to induce fracture are recorded. The cement is then allowed to heal. Typically, a self-healing cement self-repairs in about 10 to 12 hours after a fracture is formed.

Figure 9:
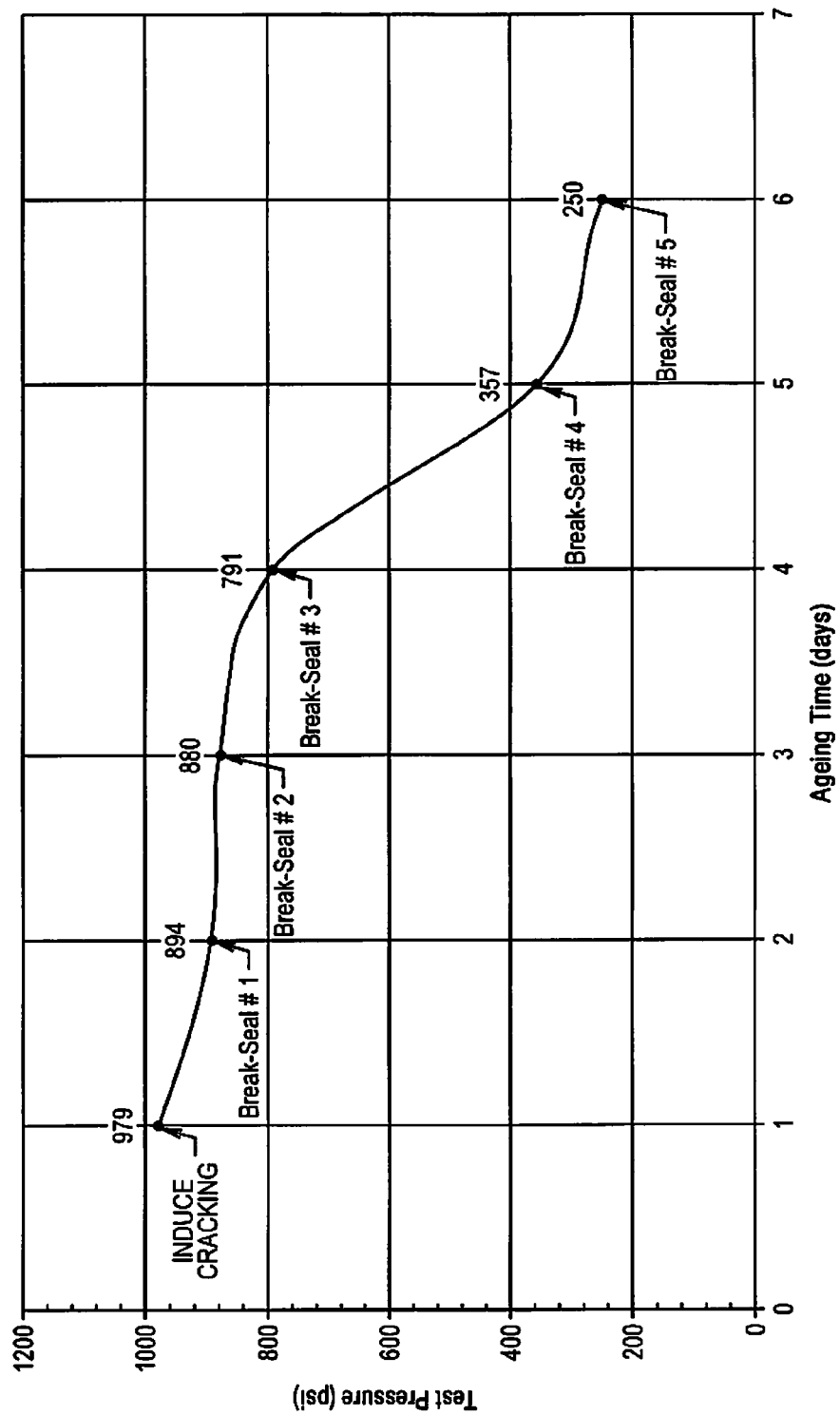
FIG. 9 depicts results of a test where the apparatus was used to monitor the ability of a self-healing cement to seal-off induced fractures over a period of time.

The effectiveness of the self healing properties of the cement is best characterized by repeatedly inducing a fracture in the cement and then allowing the cement to self-heal. An example of such a test is illustrated in FIG. 9. The amount of maximum pressure required to break the seal at each interval is determined. The number of intervals to reach a predetermined minimum compressive strength is further indicative of the self-healing properties of the cement. Since the testing apparatus described herein is capable of withstanding pressures as high as 3,000 psi, the described method provides an accurate measurement on the seal-healing capabilities of a cement while eliminating experimental errors.

Carbon dioxide gas when mixed with water forms carbonic acid which, in turn, reacts with calcium hydroxide in hydrated Portland cement to form calcium carbonate. Water is also a by-product of the reaction. The functionality of the cement typically changes as a result of the reaction. The competency of the cement to anchor the casing into the wellbore, to isolate formation fluids from migrating from one zone to another and to protect casing from corrosive fluid will slowly diminish. The apparatus can be used to test cement for testing carbon dioxide resistant cementing applications.

FIG. 2 will illustrate the corrosion rate or ability of the set cement to resist along the cement to casing interface. Using piston 30a in FIG. 3 will illustrate the ability of the set cement to resist or the corrosion rate of carbonic acid in fractured set cement. Carbonic acid is injected into test cell 12 through inlet port 14 at constant volume flow rate or constant pressure. At constant pressure test, the fluid flow rate exiting outlet port 16 is monitored. The change in flow will determine the ability of CO2 cement to resist corrosion or not. At constant flow rate test, the increase or decrease of injection pressure will determine the ability of CO2 cement to resist corrosion.

Testing apparatus 10 of FIG. 2 or FIG. 3 has particular applications in measuring the bonding strength of a set cement. The curing pressure is released and the APSR is adjusted to provide some space for the piston to travel. Hydraulic pressure is injected through the bottom port 48 at constant flow rate. The test pressure will slowly increase as the injected volume is increase. The piston movement is monitored using displacement transducer 40. The piston 30 movement along with the decrease in the testing pressure will determine when the cement breaks its bonding from to the wall of the testing cell 10. The amount of testing pressure will determine the calculated shear bond strength of the set cement to the wall of the test cell 10 using standard engineering equations. The test is all done at test temperature. Unlike conventional methods of testing bond strength where the test temperature is decreased to a safe condition to remove the set cement from a curing chamber In this method the cement remains within the test cell at test temperature for the duration of the test. As such, the testing method described herein provides more accurate results since the effects caused by cooling or temperature changes are eliminated; the data being based on actual in situ downhole temperature conditions. The bottom surface of piston 30b is positioned along the horizontal axis substantially defined by inlet port 14 and outlet port 16. Inlet port 14 and outlet port 16 are plugged and the cement slurry is poured into test cell 12. Testing the hydraulic bonding strength typically proceeds with a single pour of cement slurry. After the cement has set, the plug is removed from inlet port 14 and is replaced with a plug connector. APSR 32 is then released. Hydraulic pressure is then pumped through inlet port 14. This forces piston 30b bonded to the set cement to move upwards along the centerline axis in test cell 12 and away from the set cement. Hydraulic fluid is pumped continuously to the set cement through inlet port 14 until the hydraulic pressure drops. The positive movement of displacement transducer 40, fluid flow out of the exit port and the hydraulic pressure drop indicates the loss of cement bonding to piston 30b. The amount of force required to break the interfacial adhesion of the cement to piston 30b is recorded. The hydraulic shear strength is then calculated and expressed in pounds per square inches (psi).

The following examples are illustrative of some of the embodiments of the present invention. Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

EXAMPLES

A testing apparatus was constructed as set forth in FIG. 2. The uppermost top portion of APSR 32 had a 9/16 inch hexagonal head 33. Each face on the hexagonal head had one threaded holes or PDPLs 60 drilled into it. A 1.25 inches long limit screw (machine screw) 62 was threaded into the PDPL. Push pin 64 and push pin sleeve 66 were mounted on top cover 24. The cone surface of push pin 64 was in contact with piston 30. The proximity of push pin 64 was about 1.5 inches away from the center of top cover 16 and was secured to top cover 16 within the rotational path of the limit screw. APSR 32 was threaded through the top cover to about 1/16 to 3/16 inches below top cover 24. This entire assembly with top cover 24 was then secured to testing apparatus 10 with six bolts 26 (shown in FIG. 1). Piston 30 was inserted from the bottom end of test cell 12 until securely against the bottom of APSR 32. The complete test cell assembly without the bottom cover was dropped into a heating assembly, set forth in FIG. 4. Safety lock 74 was set to secure the testing assembly to the heating assembly chamber. At this time blank plug 23 was installed into inlet port 14 and outlet pressure port 16. The cement mixture was poured into the test cell cavity 10 to the rim. The slurry is puddled with a glass or stainless steel rod. Bottom cover 34 was then secured to the testing apparatus 10 with six 3/8 inch diameter bolt. The cement is cured at a pressure of about 3,000 psi at room temperature for about 96 hours. After curing, APSR 32 was turned counterclockwise to release the piston. The safety lock to the heating assembly was then removed and the testing assembly of FIG. 4 was then inverted by 180 degrees.

Example 1

Figure 5:
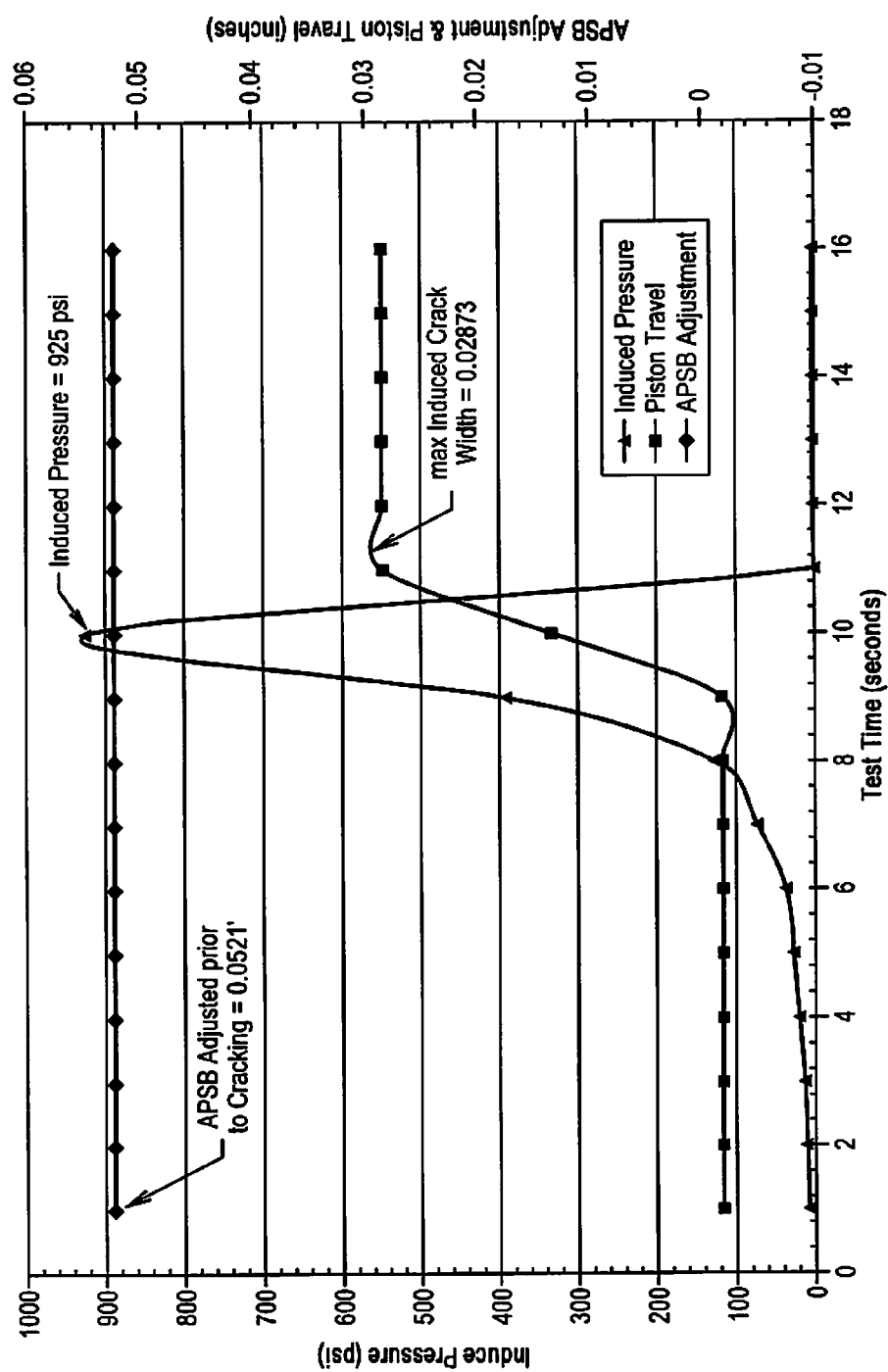
FIG. 5 depicts a control test (at atmospheric conditions) and illustrates the amount of requisite pressure needed to fracture the seal of a self-healing cement within an uncontrolled fracture width.

Using the apparatus set forth in FIG. 3 Piston Depth Position Locator (PDPL) 60 with limit screw 62 was set on location "E". The Adjustable Piston Depth-Setting Rod (APSR) 32 was adjusted prior to fracturing to its fullest maximum range of travel at location "E" (0.0521 inches"). Location "E" is the APSR setting providing the piston its deepest position and covers the maximum full range of vertical motion. After the cement was set, APSR 32 was released out to its minimum depth setting position so that the piston could travel to its full ranges. A model Q5200 QUIZIX pump was used with crude oil at control flow rate of 3.0 cc per min. As illustrated in FIG. 5, the maximum hydraulic pressure required to induce a fracture width of 0.02873 inches at flow rate of 3.0 cc per min was found to be 925 psi.

Example 2

Figure 6:
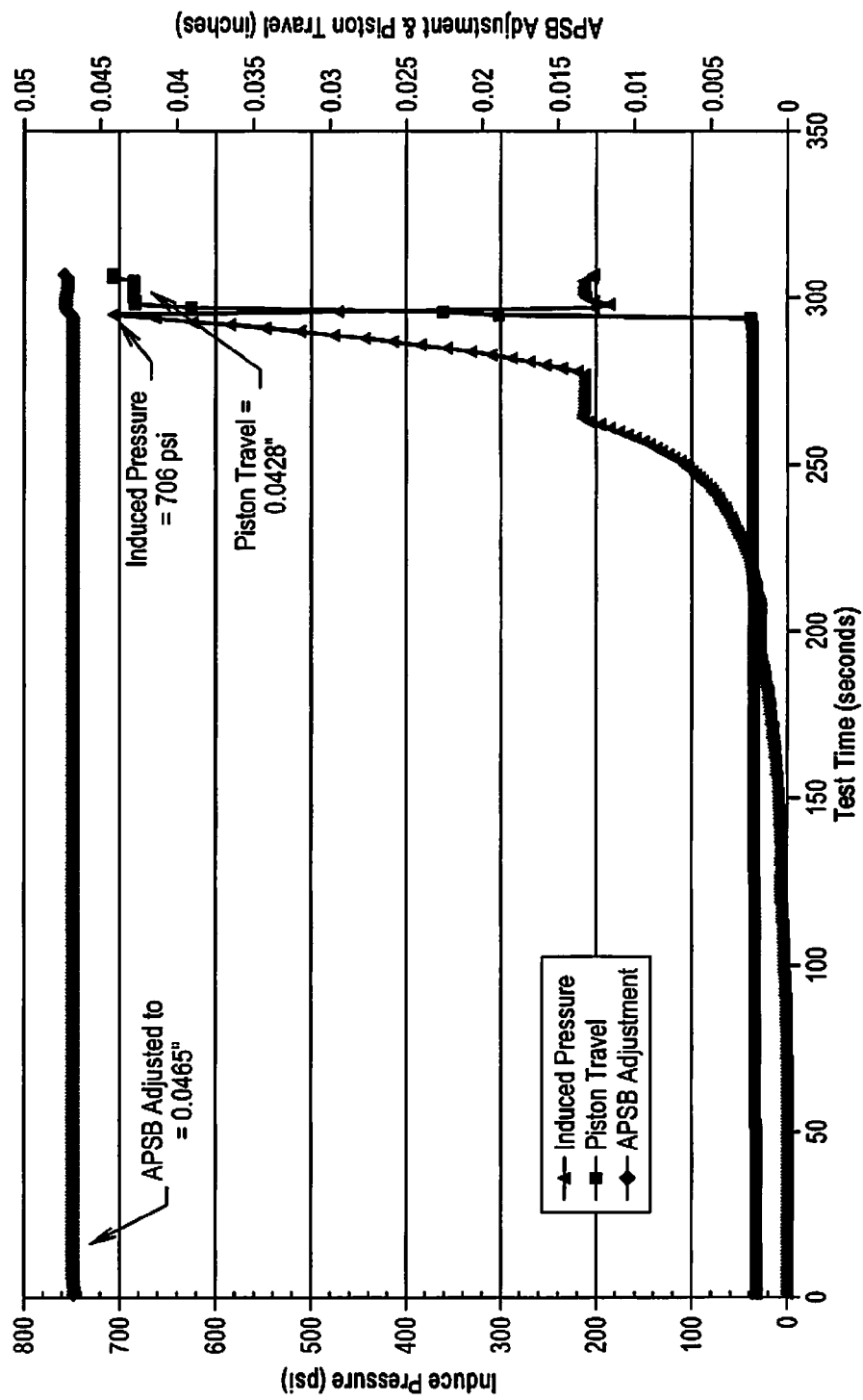
FIG. 6 depicts control of the fracture width when testing a test cement in accordance with the invention.

Using the same apparatus set forth in FIG. 3, PDPL 60 was set on location "C" (the approximate midpoint position of travel ranges). After the cement was set, APSR was released to approximately 0.0465 inches. Crude oil was pumped at a rate of about 5.0 cc per min. The induced pressure to break the sample was 706 psi and the piston traveled to 0.0428 inches. At these conditions the piston traveled all the way until it pushed against the bottom of the APSR. The data is set forth in FIG. 6. As illustrated, there was slight movement to the APSR measurement after the sample broke. This movement was due to the piston pushing the APSR while being pushed by the sample. This means that the piston was on its top dead center to the APSR. The slight movement of the APSR after inducing the sample is due to APSR thread tolerances between the bolt thread during machining FIG. 6 demonstrates the ability to control and define the width of the fracture. This is in contrast to FIG. 5 which illustrates that the width of the fracture may be uncontrolled and thus define itself Example 3

Figure 7:
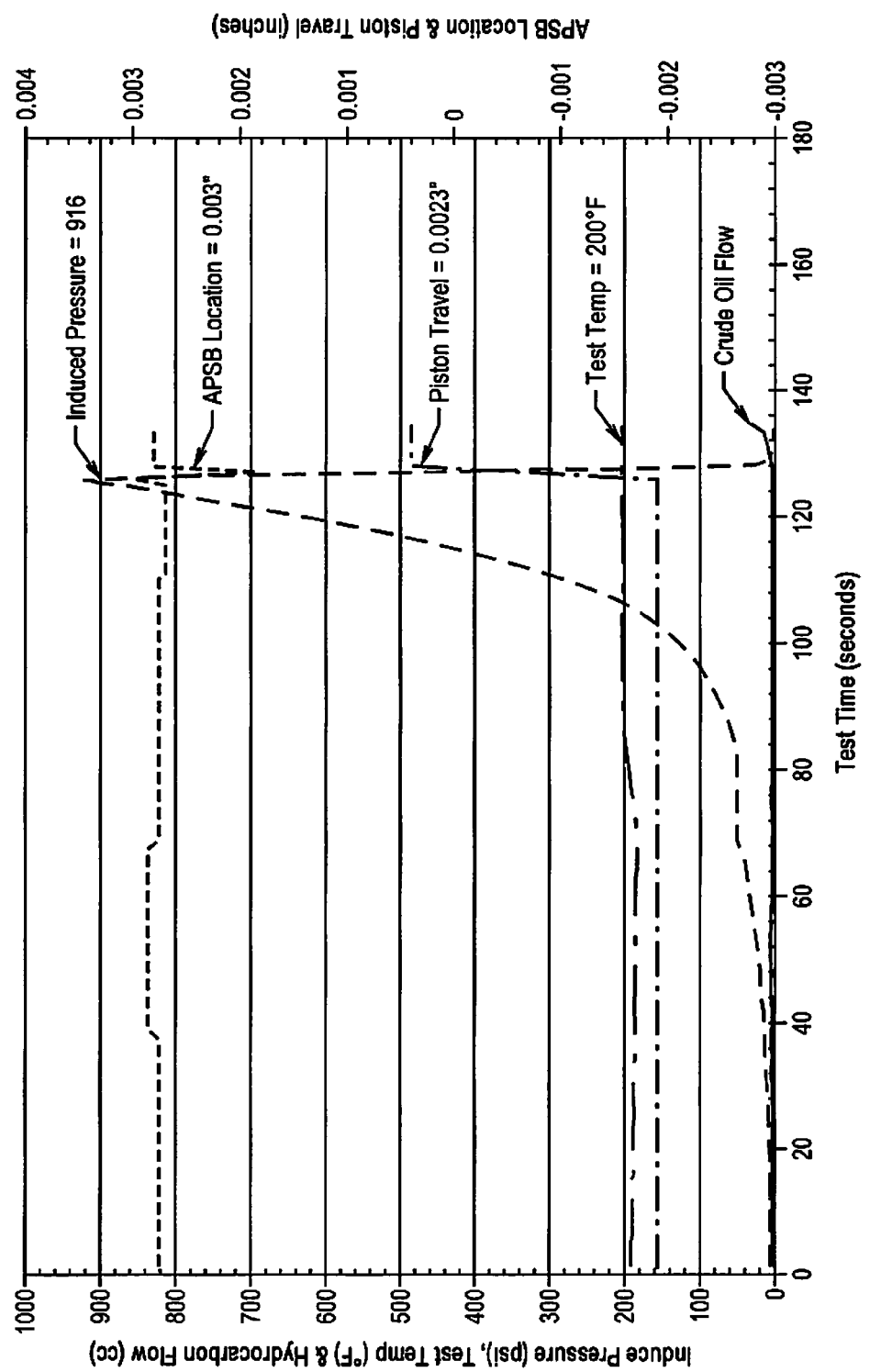
FIG. 7 depicts the amount of requisite pressure needed to fracture the set cement of a self-healing cement or other cement system under simulated temperatures and pressures at pre-determined crack width.

Example 1 was repeated except the sample was cured at 200° F. and the APSR 32 was adjusted to a controlled fracture width of 0.003 inches using displacement transducer 38. A similar fluid flow rate of 3.0 cc per min was used. The hydraulic pressure required to induce a fracture to the sample was 916 psi which is almost equal to the maximum hydraulic pressure of Example 1 while the piston travel to 0.0023 inches. The results illustrated in FIG. 7 establish that the test may be conducted under simulated temperatures and pressures.

Example 4

Figure 8:
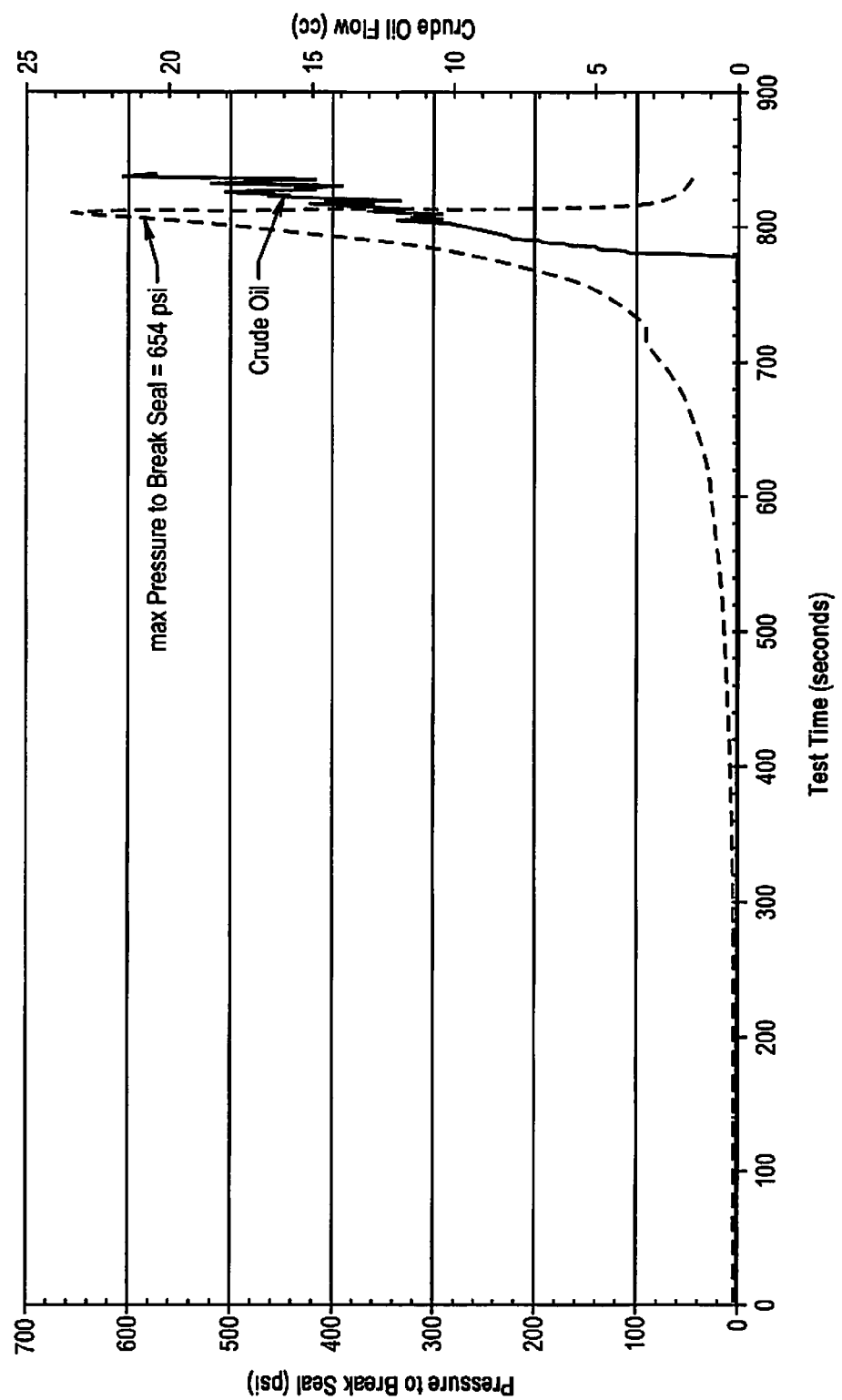
FIG. 8 depicts results of a test where the apparatus was used to monitor the performance of a self healing cement.

The cement slurry defined above and containing a self healing additive was introduced through the bottom of test cell 12. APSR 32 was adjusted to create an induced controlled fracture width of 0.013 inches. After inducing the fracture to the set cement the self-healing additive embedded in the cement matrix was allowed to react with crude oil for one day to stipulate the activation. At this time crude oil was pumped into the induced fracture at 1.0 cc per min. The APSR maintained its position and prevented any piston movement during the break-seal test. The fracture was then healed by subjecting the cement to room temperature for about 24 hours. The apparatus design prevented the inducement of a fracture from opening further as the crude oil was forced into the induced fracture. The self-healing additive embedded in the cement matrix after it had been instigated by the crude oil held crude oil flow up to 654 psi. The results are illustrated in FIG. 8 which demonstrates the ability of the testing apparatus to monitor the performance of self-healing additives in the cement mix.

Example 5

The cement slurry defined above and containing a self healing additive was introduced through the bottom of test cell 12. APSR 32 was adjusted to create an induced controlled fracture width of 0.003 inches. Crude oil at flow rate of 3.0 cc/min was used to create the desired fracture width of 0.003 inches with hydraulic pressure of 979 psi. After inducing the fracture to the set cement, the self-healing additive embedded in the cement matrix was allowed to interact with crude oil. A Break-Seal test was conducted on the induced fracture at a flow rate of 1.0 cc per min. The self-healing additive prevented the flow of crude oil across the sample up to 894 psi after one day of instigation. The cement containing the self-healing additive was then allowed to re-heal again for one day and another Break-Seal test was run after at the same fluid flow rate. The self-healing additive held back any crude oil flow up to 880 psi. The same test procedure were used on the third, fourth and fifth experiment and the breaking pressure decrease each time the sample was tested as illustrated in Table I.

TABLE 1

| Elapsed time (days) | Break Pressure (psi) |
|---|---|
| 1 | 979 |
| 2 | 894 |
| 3 | 880 |
| 4 | 791 |
| 5 | 357 |
| 6 | 250 |

On the last run the sample held up to 250 psi before releasing any crude oil to flow. FIG. 9 illustrates the ability of the self-healing additive to seal-off induced fractures by hydrocarbon fluids, breakdown the closure due to the activation of the self-healing additive and the ability for the cement to re-heal.

Example 6

Figure 10:
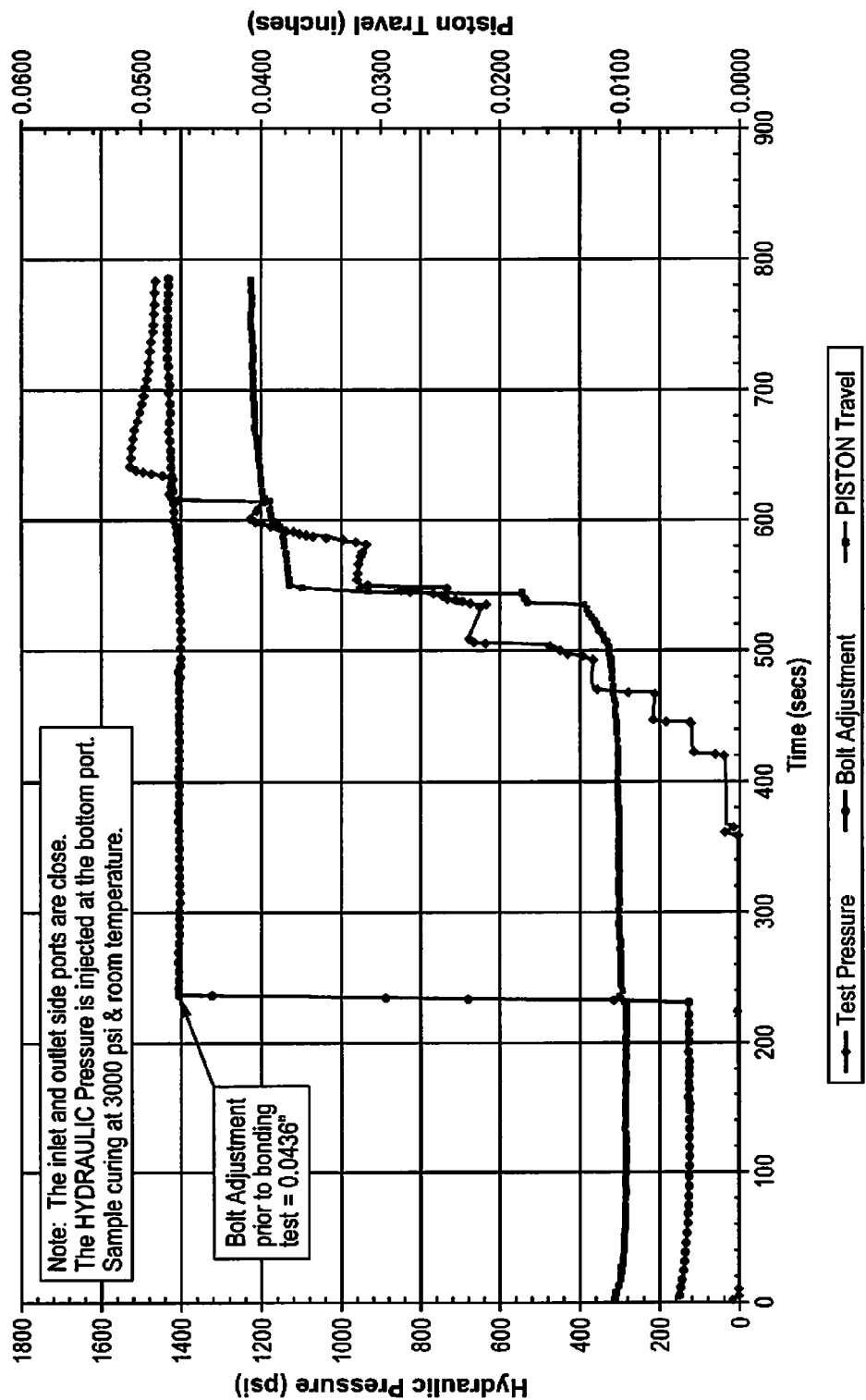
FIG. 10 depicts results of a test where the apparatus was used to determine shear bond strength of a set cement

Shear bonding of a cement was determined using the apparatus depicted in FIG. 3. The cement slurry was introduced into test cell 12 Curing pressure at about 3000 psi is injected to the sample through the bottom cover port 48 and cured at room temperature. Inlet port 14 and outlet port 16 were plugged APSR 32 was adjusted to 0.0436 inches using displacement transducer 38. Pressure was induced using water under a constant flow rate of about 3 ml/min through bottom port 48. The hydraulic pressure was slowly injected into test cell 12 and movement of piston 30a indicated when the cement broke its bonding to the wall of test cell 12. Piston movement was about 0.03 inches at about 1220 psi. After the test, the blank plugs were removed from inlet port 14 and outlet port 16 water flow was observed under pressure. Any water from the inlet port 14 and outlet port 16 will indicate water by-passed through the sample and may not be a true indication of shear strength. The water pressure was then released from the bottom cover port 48 and the top cover is removed. Piston 30a was pulled out from test cell 12 using a piston puller. If water was present between piston 30a and the top of the set cell then there was fluid by-pass between the set cement and the wall of test cell 12. If no water was present on top of the sample then the number was true shear bond strength. The shear bond strength was calculated using standard engineering formulas. The results are illustrated in FIG. 10. The amount of force required to move the cement signifies the amount of pressure required to break the seal of the cement. This value can be used then to derive the shear bond strength of the cement.

The foregoing disclosure and description of the invention is illustrative and explanatory thereof, and various changes in the size, shape, and materials, as well as in the details of illustrative construction and assembly, may be made without departing from the spirit of the invention.

What is claimed is:

1. An apparatus for testing properties of set cement comprising:
   (a) a test cell for cement;
   (b) a piston for positioning within the test cell;
   (c) an adjustable piston depth-setting rod;
   (d) a limit screw for limiting the degree of rotation of the adjustable piston depth-setting rod;
   (e) an inlet port and an outlet port on lateral walls of the test cell;
   (f) a pivot and a lockpin for inverting the test cell;
   (g) a bottom cover for positioning under the test cell and having a bottom port for entry of cement; and
   (h) a heating jacket adjacent to at least one face of the test cell.

2. The apparatus of claim 1, further comprising:
   (i) a top cover for positioning over the top of the test cell;
   (j) a piston depth position locator;
   (k) a first displacement transducer mountable into the adjustable piston depth-settling rod;
   (l) a push pin extendable through the top cover into the test cell to the top of the piston; and
   (m) a second displacement transducer mountable on the top portion of the push pin.

3. The apparatus of claim 1, further comprising a sleeve for housing the push pin.

4. The apparatus of claim 1, wherein the heating jacket surrounds the test cell.

5. The apparatus of claim 1, further comprising a pivot and a lockpin for inverting the test cell.

6. A method of testing the healing capacity of a self-healing cement comprising:
   (a) curing a self-healing cement in a test cell, the test cell having an inlet port and an outlet port;
   (b) inducing a fracture of pre-determined width in the cured self-healing cement while the cured self-healing cement is within the test cell by flowing a formation fluid under pressure into the test cell;
   (c) waiting for a time sufficient for the self-healing cement to seal the induced fracture; and
   (d) inducing a fracture of pre-determined width in the sealed self-healing cement of step (c) and measuring the hydraulic pressure required to induce the fracture while the self-healing cement is within the test cell.

7. The method of claim 6, wherein steps (c) and (d) are repeated.

8. The method of claim 6, wherein the test cell is a component of a testing apparatus, the testing apparatus further comprising a piston and an adjustable piston depth-setting rod wherein the controlled width of the test cement is set by movement of the piston by the piston depth-setting rod within the test cell apparatus.

9. The method of claim 8, wherein the testing apparatus further comprises a piston depth positioning locator.

10. A method of testing the healing capacity of a self-healing cement in a testing apparatus, the testing apparatus comprising a test cell, an inlet port, an outlet port diametrically opposite to the inlet port, a bottom port, a piston and an adjustable piston depth-setting rod, wherein the adjustable piston depth-setting rod is adjacent to the piston, the method comprising:
    (a) introducing into the test cell through the bottom port a cement slurry wherein the piston is positioned along the horizontal axis substantially defined by the inlet port and outlet port;
    (b) curing the self-healing cement in the test cell, wherein the location of the bottommost portion of the piston during curing is substantially the same as the vertical axis of the inlet port and outlet port;
    (c) defining a travel path for the piston by moving the adjustable piston depth-setting rod a set distance away from the piston;
    (d) inducing a fracture in the cured cement by flowing a formation fluid under pressure into the test cell through the inlet port, the fracture having a width defined by the travel path;
    (e) waiting for a time sufficient for the self-healing cement to seal the induced fracture; and
    (f) inducing a fracture of defined fracture width in the sealed self-healing cement of step (e) and measuring the hydraulic pressure required to induce the fracture.

11. The method of claim 10, wherein the formation fluid is crude oil, hydrocarbon gas or combinations, carbon dioxide, hydrogen sulfide gas, fresh water, brine water or steam.

12. The method of claim 10, wherein the testing apparatus further comprises a piston depth positioning locator.

13. The method of claim 10, wherein the cement slurry is introduced into the cell stage in multiple stages.

* * * * *